United States Patent [19]

Matier et al.

[11] Patent Number: 4,895,934

[45] Date of Patent: Jan. 23, 1990

[54] PROCESS FOR THE PREPARATION OF CLINDAMYCIN PHOSPHATE

[75] Inventors: William L. Matier, Hockessin, Del.; Chi Woo; Ying-Chi Lee, both of Libertyville, Ill.

[73] Assignee: E. I. Du Pont De Nemours and Company, Wilmington, Del.

[21] Appl. No.: 328,884

[22] Filed: Mar. 27, 1989

Related U.S. Application Data

[62] Division of Ser. No. 234,717, Aug. 22, 1988, Pat. No. 4,849,515.

[51] Int. Cl.$^4$ ............................................. C07H 15/16
[52] U.S. Cl. ................................. 536/16.5; 536/16.2
[58] Field of Search ............................. 536/16.2, 16.5

[56] References Cited

U.S. PATENT DOCUMENTS

| | | | |
|---|---|---|---|
| 3,487,068 | 12/1969 | Morozowich et al. | 536/16.5 |
| 3,496,163 | 2/1970 | Birkenmeyer et al. | 536/16.5 |
| 3,856,943 | 12/1974 | Birkenmeyer et al. | 536/16.5 |
| 3,892,729 | 7/1975 | Birkenmeyer et al. | 536/16.5 |
| 4,430,495 | 2/1984 | Patt et al. | 536/16.5 |

*Primary Examiner*—Joseph L. Schofer
*Assistant Examiner*—Gary L. Kunz
*Attorney, Agent, or Firm*—Gildo E. Fato

[57] ABSTRACT

A method for the preparation of clindamycin phosphate by first preparing the novel intermediate, clindamycin phosphoryl benzylate. The method can be used to make other, structurally related compounds.

5 Claims, No Drawings

PROCESS FOR THE PREPARATION OF CLINDAMYCIN PHOSPHATE

This application is a division of application Ser. No. 07/234,717, filed 08/22/88, now U.S. Pat. No. 4,849,515.

BACKGROUND OF THE INVENTION

Clindamycin, 7(S)-chloro-7-deoxylincomycin, the preparation of which is described in U.S. Pat. No. 3,487,068 issued Dec. 30, 1969, is a potent antibacterial agent. Clindamycin is a derivative of the amino acid trans-L-4-n-propylhygrinic acid, attached to a sulfur-containing derivative of an octose.

Clindamycin and lincomycin bind exclusively to the 50 S subunit of bacterial ribosomes and suppress protein synthesis. Although clindamycin, erythromycin and chloramphenicol are not structurally related, they all act at this site, and the binding of one of these antibiotics to the ribosome may inhibit the reaction of the other. In general, clindamycin is similar to erythromycin in its activity in vitro against pneumococci, Strep. pyogenes, and viridans streptococci. Almost all such bacterial strains are inhibited by concentrations of 0.04 µg/mL. It is also active against many strains of Staph. aureus but may not inhibit methicillin-resistant strains. Clindamycin is nearly completely absorbed following oral administration, and peak plasma concentrations of 2 to 3 µg/mL are attained within 1 hour after the ingestion of 50 mg. The presence of food in the stomach does not reduce absorption significantly. The half-life of the antibiotic is about 2.5 hours, and modest accumulation of drug is to be expected if it is given at 6 hour intervals. The phosphate ester of clindamycin which is given parenterally, is also rapidly hydrolyzed in vivo to the active parent compound. Following intramuscular injection, peak concentrations in plasma are not attained for 3 hours in adults and 1 hour in children. The recommended parenteral dosages provide peak plasma concentrations of 5 to 15 µg/mL and effective antimicrobial activity for approximately 8 hours. Most of the drug is inactivated by metabolism to N-demethylclindamycin and clindamycin sulfoxide, which are excreted in the urine and bile. The half-life of clindamycin is lengthened only slightly in patients with markedly impaired renal function, and little adjustment of dosage is required for such individuals.

DETAILED DESCRIPTION OF THE INVENTION

In accordance with one embodiment of the present invention, clindamycin phosphate is prepared by first preparing the novel clindamycin phosphoryl benzylate. Preparation of clindamycin phosphate by means of this intermediate, which can be easily isolated and purified, eliminates the need for use of column chromatography. For example, see U.S. Pat. No. 3,487,068 issued Dec. 30, 1969, particularly Examples 1 and 2 wherein lincomycin-2-phosphate and 7(S)-chloro-7-deoxylincomycin-2-phosphate are purified by column chromatography. In a specific embodiment of the invention, this monophosphate benzyl ester is prepared by treating protected clindamycin hydrochloride with phosphorus oxychloride in the presence of a suitable solvent to obtain a reaction mixture, adding benzyl alcohol to the reaction mixture and subsequently adding water to complete the reaction. In this reaction, the benzyl alcohol is not only a reactant but also a powerful solvent in which the desirable intermediate is freely soluble. Moreover, any by-products are easily removed by washing with an aqueous solution.

The overall process of the invention can be depicted by the following reaction scheme.

Reaction Sequence

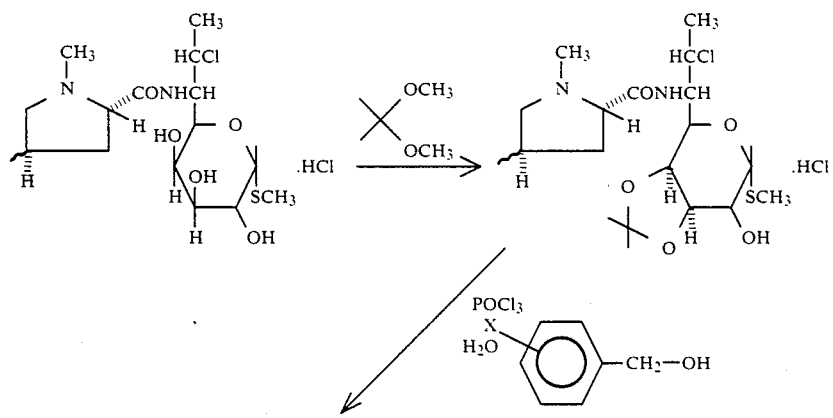

-continued
Reaction Sequence

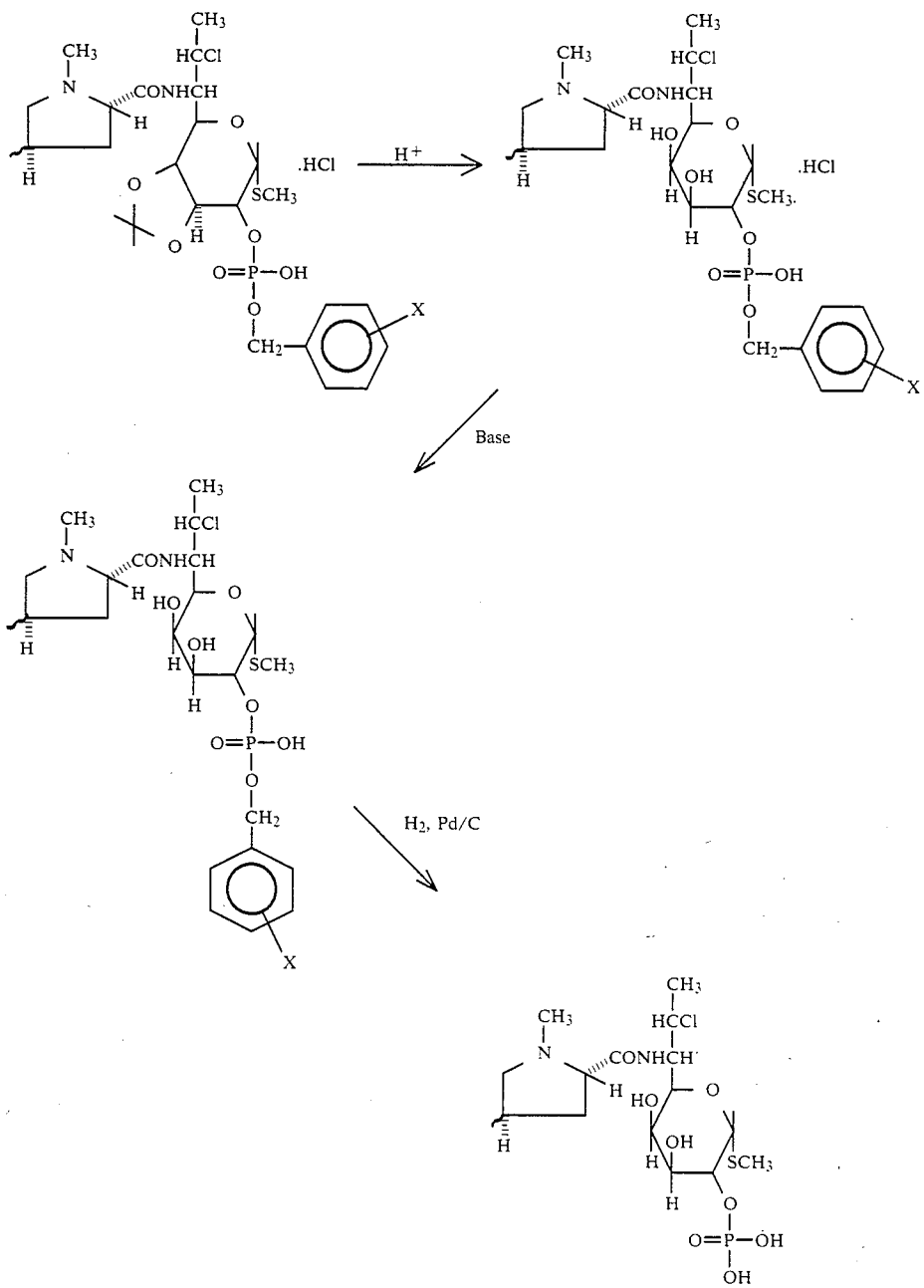

X = H, loweralkyl, halo, loweralkoxy, —NO₂, —CF₃, or phenyl

EXAMPLE 1

SYNTHESIS OF CLINDAMYCIN HCL

Summary of Process

Hexachloroethane (306 g) (Note) is suspended in 1,2-dichloroethane (100 mL) and the suspension is cooled. Triphenyl-phosphine (312 g) dissolved in 1,2-dichloroethane (500 mL) is added slowly and stirring is continued to ensure complete formation of the Rydon reagent.

DMF (100 mL) is then added and the resulting yellow solution is stirred for 1 hour before the addition of lincomycin HCl (100 g). The mixture is heated and agitated for several hours, cooled and hydrolyzed. A series of acid/base extractions is then employed to remove the by-product triphenylphosphine oxide. Clindamycin HCl (73–78 g; 70–75%) is finally crystallized from ethanol. Melting point: 132° to 133° C. NOTE: Hexachlorothane is used as the source of chlorine to form the Rydon reagent, triphenylphosphinedichloride.

EXAMPLE 2

CLINDAMYCIN PHOSPHATE

General Description of Manufacturing Method

STEP I: Preparation of protected clindamycin hydrochloride

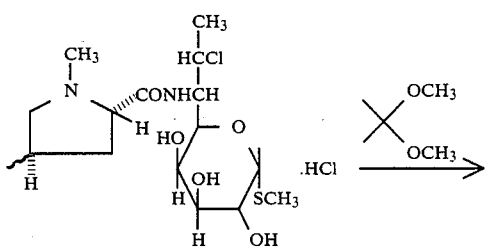

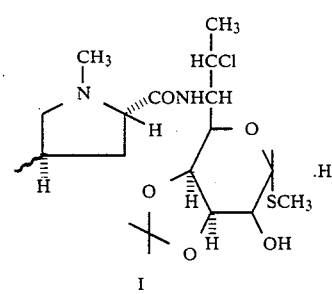

Clindamycin hydrochloride is heated with 2,2-dimethoxy-propane in a suitable solvent. Upon cooling, the protected clindamycin hydrochloride, I, is isolated by filtration. Melting point: 162° to 163° C.

EXAMPLE 3

STEP II: Preparation of protected clindamycin benzylate hydrochloride

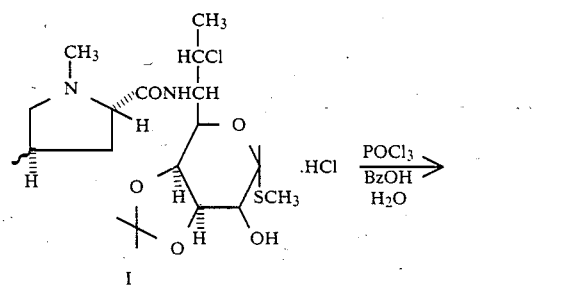

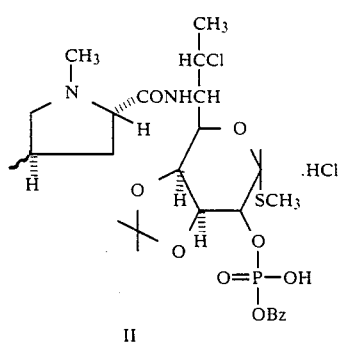

The protected clindamycin hydrochloride, I, is treated with phosphorous oxychloride in a suitable solvent, such as pyridine, at sub-ambient temperatures. Benzyl alcohol is added slowly then the reaction mixture is allowed to warm to room temperature. Water is then added slowly, and the reaction mixture is stirred for a period of time at room temperature. After separation of the aqueous layer, the organic layer is washed and dried; crystallization of the product is affected by the addition of a suitable solvent, such as acetone, to the organic layer. The protected clindamycin hydrochloride, II, is isolated by filtration. Melting point: 254° to 258° C.

EXAMPLE 4

STEP III: Preparation of deprotected clindamycin benzylate hydrochloride

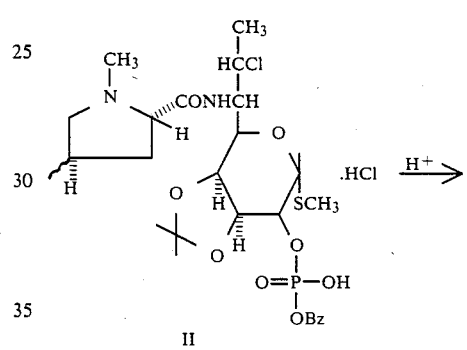

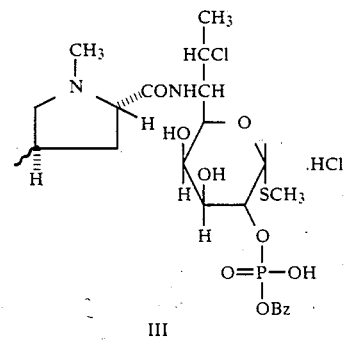

The protected clindamycin benzylate hydrochloride, II, is heated with acid (i.e. aqueous hydrochloric acid) in a suitable solvent such as methanol. Water is added slowly to precipitate the product then a portion of the solvent distilled off. Upon cooling the deprotected clindamycin benzylate hydrochloride, III, is isolated by filtration.

EXAMPLE 5

STEP IV: Preparation of clindamycin benzylate free base

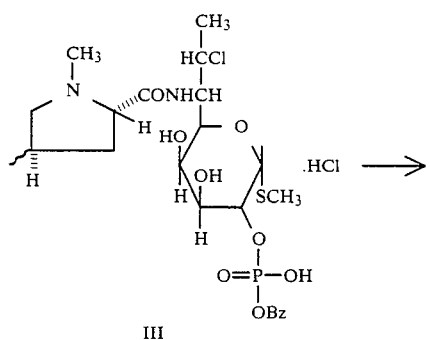

III

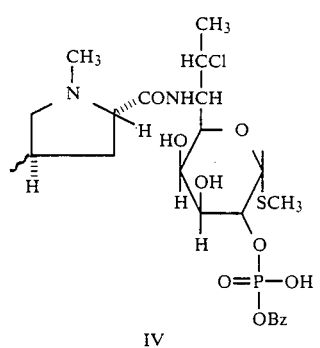

IV

Deprotected clindamycin benzylate hydrochloride, III, is treated with a suitable base such as ammonium hydroxide in water. Neutralization of the solution with a suitable acid (i.e. aqueous hydrochloric acid) precipitates clindamycin benzylate free base, IV, which is isolated by filtration. Melting point: 218° to 220° C.

EXAMPLE 6

STEP V: Preparation of clindamycin phosphate

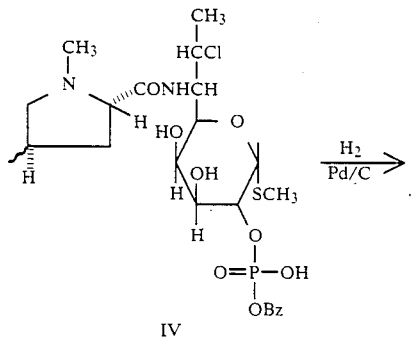

IV

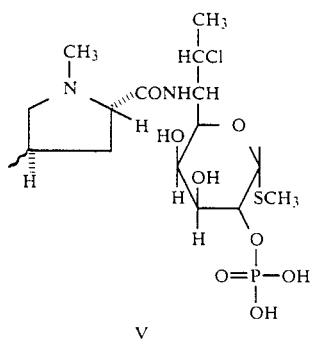

V

Treatment of clindamycin benzylate free base, IV, with hydrogen gas in the presence of Pd/C catalyst in a suitable solvent (i.e. methanol, water or a methanol/water mixture) gives clindamycin phosphate, V. Following the completion of the hydrogenolysis, the water/methanol solvent ratio may be adjusted and a portion of a suitable co-solvent such as acetonitrile may be added. The reaction mixture is heated to ensure dissolution of product, then filtered to remove the catalyst. Additional acetonitrile is added to the filtrate, which is then cooled, to effect crystallization of the product. The clindamycin phosphate, V, is isolated by filtration.

If required, this material may be purified by recrystallization, following charcoal treatment if necessary, from a suitable solvent system (i.e. water, methanol, acetonitrile or a mixture of these solvents). Melting point: 208° to 212° C.

What is claimed is:

1. A process for the preparation of 7(S)-chloro-7-deoxylincomycin-2-phosphoryl benzylate, said process comprising:
   treating protected clindamycin hydrochloride with phosphorous oxychloride in the presence of a suitable solvent to obtain a reaction mixture;
   adding benzyl alcohol to the reaction mixture; and
   subsequently adding water to the reaction mixture to obtain the product.

2. A process for the preparation of a compound having the formula:

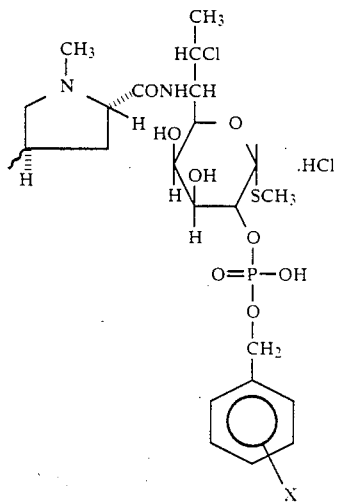

wherein X is hydrogen, loweralkyl, halo, loweralkoxy, nitro, —CF$_3$ or phenyl, said process comprising: treating protected clindamycin hydrochloride with phosphorous oxychloride in the presence of a suitable solvent to obtain a reaction mixture; adding benzyl alcohol, unsubstituted or substituted with loweralkyl, halo, loweralkoxy, nitro, —CF$_3$ or phenyl to the reaction mixture, provided that said benzyl alcohol is unsubstituted when X is hydrogen and when substituted, the substituent is the same as X; and subsequently adding water to the reaction mixture to complete the reaction.

3. The process of claim 2 wherein X is hydrogen, loweralkyl or halo.

4. The process of claim 3 wherein X is hydrogen.

5. A process for the preparation of clindamycin phosphate, said process comprising:

treating protected clindamycin hydrochloride with phosphorous oxychloride in a suitable solvent to obtain a reaction mixture;

adding benzyl alcohol to the reaction mixture and subsequently adding water to complete the reaction and thereby obtaining protected clindamycin benzylate, hydrochloride;

heating the protected clindamycin benzylate hydrochloride in the presence of an acid to obtain deprotected clindamycin hydrochloride;

isolating the deprotected clindamycin benzylate hydrochloride;

treating the deprotected clindamycin benzylate hydrochloride with a suitable base to obtain clindamycin benzylate free base;

isolating the clindamycin benzylate free base; and treating the clindamycin free base with hydrogen gas in the presence of Pd/C catalyst in a suitable solvent to thereby obtain clindamycin phosphate.

* * * * *